US008093290B2

(12) United States Patent
Galopin et al.

(10) Patent No.: US 8,093,290 B2
(45) Date of Patent: Jan. 10, 2012

(54) COOLANT SOLUTIONS AND COMPOSITIONS COMPRISING THE SAME

(75) Inventors: Christophe Galopin, Cincinnati, OH (US); Eduardo Moraes, Egg b. Zürich (CH); Lori Tigani, Cincinnati, OH (US)

(73) Assignee: Givaudan SA, Vernier (CH)

( * ) Notice: Subject to any disclaimer, the term of this patent is extended or adjusted under 35 U.S.C. 154(b) by 1965 days.

(21) Appl. No.: 10/532,514

(22) PCT Filed: Oct. 27, 2003

(86) PCT No.: PCT/CH03/00703
§ 371 (c)(1),
(2), (4) Date: Apr. 25, 2005

(87) PCT Pub. No.: WO2004/037764
PCT Pub. Date: May 6, 2004

(65) Prior Publication Data
US 2006/0051301 A1    Mar. 9, 2006

Related U.S. Application Data

(60) Provisional application No. 60/421,673, filed on Oct. 28, 2002.

(51) Int. Cl.
A61K 8/00 (2006.01)
A61K 8/37 (2006.01)
A61K 8/33 (2006.01)
A61Q 11/00 (2006.01)

(52) U.S. Cl. ........ 514/529; 514/546; 514/621; 426/534; 424/401; 424/49

(58) Field of Classification Search .................. 514/529, 514/546, 621; 424/49, 401
See application file for complete search history.

(56) References Cited

U.S. PATENT DOCUMENTS

| 5,783,725 A | 7/1998 | Kuhn et al. .................. 560/188 |
| 6,627,233 B1 * | 9/2003 | Wolf et al. ........................ 426/3 |
| 2004/0018954 A1 * | 1/2004 | Su et al. ............................ 512/1 |

FOREIGN PATENT DOCUMENTS

| DE | 196 07 278 A | 8/1997 |
| GB | 1 351 761 A | 5/1974 |
| WO | WO 99/13734 A | 3/1999 |

OTHER PUBLICATIONS

H&R, Frescolat Cooling Ingredients, pp. 1-13, 1999.*
Chemical Book, http://www.chemicalbook.com/ChemicalProductProperty_EN_CB0252522.htm, retrieved Aug. 29, 2009.*
New World Encyclopedia, "Solvent", pp. 1-5, retrieved Feb. 12, 2011.*
Wang et al. "Eutectic Composition of a Chiral Mixture Containing a Racemic Compound", Organic Process Research and Development, 9 pgs. 670-676, 2005.*
Draelos, Z. D., Cosmetic Dermatology: Products and Procedures p. 64, retrieved Feb. 23, 2011 (number of pages submitted 3).*
International Search Report dated Feb. 3, 2004 for Application PCT/CH03/00703.

* cited by examiner

*Primary Examiner* — Frederick Krass
*Assistant Examiner* — Lezah Roberts
(74) *Attorney, Agent, or Firm* — Norris McLaughlin & Marcus PA

(57) ABSTRACT

A solution consisting essentially of menthyl lactate and menthol carboxamide dissolved in a solvent, such as propylene glycol, which solvent is acceptable for food, oral care or cosmetic products and a method of preparing it.

9 Claims, No Drawings

COOLANT SOLUTIONS AND COMPOSITIONS COMPRISING THE SAME

This invention is concerned with compositions, and especially solutions comprising menthyl lactate and menthol carboxamide.

Menthyl lactate is an important ingredient that is valued for its coolant properties. Furthermore, given its virtual lack of odour and colour, it can be used in all manner of flavour and fragrance compositions to impart an intense and persistent cooling effect without affecting the balance of the fragrance or flavour accord.

It is commercially available as a white, low-melting point solid that is supplied as a solid mass that has to be physically broken down and melted before use in food or cosmetic applications. These physical properties make this compound difficult to work with. Consequently, attempts have been made in the art to provide the compound in a more convenient form. For example, in DE 19607278, reference is made to the problems of working with menthyl lactate and a new crystalline form of the material is disclosed as a solution to this problem. In this reference, it is disclosed that menthyl lactate can be mixed with a small amount of alkali or alkaline earth carbonate and recrystallised from acetone to provide menthyl lactate in fine crystal form. This crystalline form of menthyl lactate is currently commercially available. However, use of this crystalline form is not without problems.

Firstly, it is powder-like and, as with all powders, it must be handled with caution to avoid dust hazards associated therewith. Secondly, it is not always convenient or easy to mix the powder into food or into cosmetic formulation bases, which may be in a liquid or a paste-like form. To deal with this problem, formulators may solubilise the crystals using an acceptable solvent, before adding the solution to such a food product, oral care product or cosmetic product. However, this solubilization constitutes an extra processing step for the formulator, making it inconvenient and more costly to use. Thirdly, even though the menthyl lactate is provided in crystalline form, because of its low melting point, under certain storage conditions such as elevated temperature and/or high humidity, the crystalline menthyl lactate powder has a tendency to agglomerate. Therefore, for long term storage of the crystal form, it must be kept at relatively low temperatures and under conditions of low humidity.

Accordingly, there remains a need to provide menthyl lactate in a form that is easy to use in further formulation operations and which remains stable in that form for long periods of storage, even under conditions of relatively high humidity and temperature.

Surprisingly, it has now been found that stable solutions of menthyl lactate can be obtained comprising a relative high amount of menthyl lactate, if the menthyl lactate is combined with, or co-dissolved with menthol carboxamide.

Therefore, in a first aspect the present invention provides a method of preparing a solution containing menthyl lactate, wherein the final menthyl lactate concentration is higher than that achievable by dissolving menthyl lactate in a neat solvent, by
  a) liquefying menthyl lactate, and
  b) combining the liquefied menthyl lactate with menthol carboxamide and the solvent, which solvent is acceptable for food, oral care or cosmetic use.

In a second aspect the present invention refers to a solution consisting essentially of menthyl lactate and menthol carboxamide dissolved in a solvent, prepared by a method described above. Preferably, the solution of the invention does not contain any other flavour or fragrance compounds with exception of the solvent.

The solutions of the invention exhibit good storage stability. It has been observed that neither the menthyl lactate nor menthol carboxamide precipitates from the solution, even at relatively low storage temperatures, for example, down to about 4° C. Thus, a composition can be provided having a high concentration of the combined menthyl lactate and menthol carboxamide without having the aforementioned problems of solid products. Further, because the composition is in liquid form, it is considerably easier to formulate a product containing the solution, particularly a food product, an oral care product or a cosmetic product, than by using a powder or other solid mass which should be melted prior to use. Additionally, menthol carboxamide itself is known to the art to be a commercially-available coolant material, which exhibits little or no odour or flavour.

Preferred solvents for use in the present invention may be selected from any of those solvents that may be used in food, oral care or cosmetic applications. Most preferred as solvents are those selected from the group consisting of octyldodecanol, dipropylene glycol, propylene glycol, triglyceride, isopropyl myristate, olive oil, almond oil, hexyl laurate, alcohols, and mixtures thereof, as well as aqueous compositions containing one or more of the aforesaid solvents, (e.g. an aqueous alcoholic mixture containing 10% water).

As used herein, "solvent" means a single solvent or a mixture of solvents. Different purity grades, such as food-grade and pharmaceutical-grade, are included.

As used herein, "neat solvent" means a solvent as defined above not comprising menthol carboxamide.

As used herein, "liquefying" means a process step to make the solid menthyl lactate liquid by melting.

The menthyl lactate and menthol carboxamide may be added to an appropriate solvent to produce solutions containing from 1 to 99% by weight of the combined menthyl lactate and menthol carboxamide compounds, preferably 55% to 80% by weight, with the remaining balance being the solvent. More preferably, the inventive solutions contain from about 25 to 30% solvent, more particularly 27 to 29% solvent, with the remaining balance to 100% being the combined menthyl lactate and menthol carboxamide.

The ratio of menthyl lactate to menthol carboxamide may vary widely, dependent on the cooling properties sought. For example, whereas both compounds are known for their pronounced, or "high-impact" coolant effects, they have been observed to affect areas of the oral cavity differently. Menthyl lactate tends to target the front/middle of the mouth, whereas menthol carboxamide tends to target the back and roof of the mouth. The skilled formulator in the art is therefore able to combine an appropriate ratio of menthyl lactate to menthol carboxamide so to achieve any desired sensory effect as a matter of routine or by a few routine experiments, without recourse to inventive activity.

In a particularly preferred embodiment, there is provided a shelf stable-solution of menthyl lactate and menthol carboxamide containing 10% to 20% by weight menthol carboxamide, more particularly 14% to 18% by weight menthol carboxamide.

In a particularly preferred embodiment there is provided a shelf-stable solution of menthyl lactate and menthol carboxamide containing 50% to 60% by weight of menthyl lactate, more particularly 55% to 60%, especially 55% to 57% by weight menthyl lactate.

The solutions of the present invention may be formed by combining menthyl lactate and menthol carboxamide and dissolving these compounds in one or more suitable solvents, particularly one or more of the preferred solvents recited herein. Conveniently, menthyl lactate solid is first liquefied or melted at a temperature of about 40° C. to 50° C. Menthol carboxamide, which is often commercially provided as fine powder, may be directly dissolved in the liquefied menthyl lactate. Thereafter, the combined menthyl lactate/menthol carboxamide is dissolved in the solvent under suitable stirring to form shelf stable solutions therefrom.

Alternatively, the solution of the present invention is formed by dissolving menthol carboxamide in the solvent and thereafter, the liquefied menthyl lactate is combined with the menthol carboxamide solution under suitable stirring to form shelf-stable solutions therefrom.

As stated hereinabove, the solutions of the present invention are provided in a liquid form that exhibits good shelf stability with little or no precipitation. This renders the solutions easy to store under conditions of varied humidity and temperature such as about 4° C. to 25° C. preferably to 20° C., and also renders them easy to handle and to formulate into all manner of food, oral care and cosmetic products. Solutions according to the present invention are therefore eminently suitable for admixture with food, oral care and cosmetic products in order to produce products with desirable cooling effects.

Accordingly, a further aspect of the present invention refers to a method of improving the solubility of menthyl lactate by liquefying menthyl lactate and combining the liquefied menthyl lactate with menthol carboxamide and a solvent.

Furthermore, it has surprisingly been found that the cooling effects of the combined menthyl lactate and menthol carboxamide solutions taught herein are often not merely additive. It has been unexpectedly found that, when solutions of the present invention were tested by trained panelists in sensory evaluations against the individual menthyl lactate or menthol carboxamide compounds, synergistic cooling effects were often observed. This surprising effect is more fully described in the Examples presented below.

A further aspect of the invention is a food, oral care or cosmetic product to which has been added a solution prepared according to the first aspect of the invention. Such food, oral care or cosmetic products may be provided with the solution according to the present invention by any useful method, e.g., by simple addition to, and mixing into the food, oral care or cosmetic product of a useful amount of the solution according to the present invention.

The solutions of the present invention may be employed in a wide variety of food or oral care products, e.g., toothpastes, mouthwashes, chewing gums, confections, as well as in beverages. The solutions of the present invention may also be employed in cosmetic products, for example, products for topical application such as shaving lotions, foams, creams, gels, after-shaves, shampoos, shower gels, foam baths and other compositions known for topical use.

For use in food and oral care products, the solutions of the present invention may be employed at levels sufficient to attain a combined amount of menthyl lactate and menthol caroboxamide of about 0.01% to 1% by weight, preferably from 0.06% to 0.5%, more preferably from about 0.06% to 0.45% by weight, based on the total weight of the food or oral care product. For use in cosmetic products, the solutions of the present invention may be employed at levels sufficient to attain a combined amount of menthyl lactate and menthol carboxamide of about 0.01% to 10% by weight, based on the total weight of the cosmetic product. However, it is understood that the skilled person may employ the inventive solutions in amounts outside the aforementioned ranges to achieve sensorial effects as may be desired.

The following examples illustrate various aspects of the invention.

EXAMPLE 1

57 parts by weight of menthyl lactate are warmed to 40-50° C. to liquefy the menthyl lactate. 14 parts by weight of menthol carboxamide are mixed into the liquefied menthyl lactate. Thereafter, the menthyl lactate/menthol carboxamide mixture is added to 29 parts by weight of propylene glycol (USP) in order to form a solution of menthyl lactate and menthol carboxamide in propylene glycol.

The solution is allowed to cool and is stored. No precipitation is observed.

EXAMPLE 2

The procedure of Example 1 is carried out using 18 parts by weight of menthol carboxamide, 55 parts by weight of menthyl lactate and 27 parts by weight of propylene glycol (USP). A solution is obtained that upon cooling and storage does not produce a precipitate.

COMPARATIVE EXAMPLE 1

To illustrate the precipitation of menthyl lactate in a solvent, a 50% by weight solution of menthyl lactate was produced by first melting the menthyl lactate by heating to 40° C.-50° C., and thereafter mixing it with an appropriate amount of propylene glycol (USP). Upon cooling, a fine precipitate of menthyl lactate is observed.

EXAMPLE 3

The procedure of Example 1 is carried out using 5 parts by weight of menthol carboxamide, 65 parts by weight of menthyl lactate and 30 parts by weight of ethanol solution containing 10% by weight water. A solution is obtained that upon cooling and storage does not produce a precipitate.

COMPARATIVE EXAMPLE 2

To illustrate the precipitation of menthyl lactate in a solvent, a 60% by weight solution of menthyl lactate was produced by first melting the menthyl lactate by heating to 40° C.-50° C., and thereafter mixing it with an appropriate amount of ethanol solution containing 10% by weight water. Upon cooling in the fridge overnight, a fine precipitate of menthyl lactate is observed.

EXAMPLE 4

A sensory test was carried out with a group of 10 trained panelists in order to evaluate the performance of the solutions of Example 1 and 2 as cooling agents. Panelists were asked to assess the intensity of coolant effect at certain time periods on a line scale of zero to one hundred. Panelists held toothpaste containing formulations of Example 1 (0.65% by weight based on total amount of the toothpaste) and Example 2 (0.45% by weight based on the total amount of the toothpaste) in their mouths for 90 seconds before spitting and rinsing. Panelists record the coolant sensation at rinse (time zero), 30 s, 60 s, 90 s, 2 min, 3 min, 4, min, 5 min, 10 min, 15 min, 20 min, 25 min and 30 min.

Toothpastes containing a solution produced according to example 1 or example 2 both outperformed toothpastes containing only menthyl lactate or containing only menthol carboxamide.

The invention claimed is:

1. A method of preparing a solution consisting of menthyl lactate, menthol carboxamide and a solvent selected from propylene glycol, ethanol, and an ethanol solution which contains 10% wt. water, wherein the final concentration of menthyl lactate is higher than that achievable by dissolving menthyl lactate in a neat solvent selected from propylene glycol and ethanol, by:
   liquefying menthyl lactate; and
   combining the liquefied menthyl lactate with menthol carboxamide and the solvent.

2. A solution of menthyl lactate, menthol carboxamide and a solvent selected from propylene glycol, ethanol, and an ethanol solution which contains 10% wt. water, prepared by the method of claim 1.

3. A solution consisting of menthyl lactate and menthol carboxamide dissolved in a solvent selected from propylene glycol, ethanol, and an ethanol solution which contains 10% wt. water, characterized in that the final concentration of menthyl lactate is higher than that achievable by dissolving menthyl lactate alone in the solvent.

4. A solution according to claim 2 wherein the propylene glycol is present in amounts of 25% to 30% by weight of the total solution.

5. A solution according to claim 2 wherein the menthyl lactate is present in amounts of from 50% to 60% by weight of the total solution.

6. A solution according to claim 2 wherein the menthol carboxamide is present in amounts of from 10% to 20% by weight of the total solution.

7. The method according to claim 1, wherein the solvent is selected from propylene glycol, and an ethanol solution containing 10% wt. water.

8. The solution according to claim 2, wherein the solvent is selected from propylene glycol, and an ethanol solution containing 10% wt. water.

9. The solution according to claim 3, wherein the solvent is selected from propylene glycol, and an ethanol solution containing 10% wt. water.

* * * * *